US00PP24479P2

(12) United States Plant Patent
Kristensen

(10) Patent No.: US PP24,479 P2
(45) Date of Patent: May 20, 2014

(54) ***OSTEOSPERMUM* PLANT NAMED 'SAKOST8330'**

(50) Latin Name: *Osteospermum hybrida*
Varietal Denomination: SAKOST8330

(71) Applicant: Sakata Ornamentals Europe A/S, Marslev (DK)

(72) Inventor: Niels G. Kristensen, Silkeborg (DK)

(73) Assignee: Sakata Ornamentals Europe A/S, Marslev (DK)

( * ) Notice: Subject to any disclaimer, the term of this patent is extended or adjusted under 35 U.S.C. 154(b) by 0 days.

(21) Appl. No.: 13/986,017

(22) Filed: Mar. 22, 2013

(51) Int. Cl.
*A01H 5/00* (2006.01)

(52) U.S. Cl.
USPC ..... Plt./360

(58) Field of Classification Search
USPC ..... Plt./360
See application file for complete search history.

(56) References Cited

U.S. PATENT DOCUMENTS

PP21,087 P2 * 6/2010 Kristensen ..... Plt./360

* cited by examiner

*Primary Examiner* — Anne Grunberg
*Assistant Examiner* — Keith Robinson
(74) *Attorney, Agent, or Firm* — James M. Weatherly; Cochran Freund & Young LLC

(57) ABSTRACT

A new *Osteospermum* plant particularly distinguished by having pure clean white ray florets and blue disc florets with medium sized flower and a compact, mounding and well branching plant growth habit is disclosed.

1 Drawing Sheet

Genus and species: *Osteospermum hybrida.*
Variety denomination: 'SAKOST8330'.

BACKGROUND OF THE NEW PLANT

The present invention comprises a new and distinct variety of *Osteospermum*, botanically known as *Osteospermum hybrida*, and hereinafter referred to by the variety name 'SAKOST8330'. 'SAKOST8330' originated from a hybridization of *Osteospermum* proprietary breeding line 'Akzawhir' also known as CAPE DAISY™ 'Zanzibar White with Ring' (unpatented) and *Osteospermum* line 'Kakegawa AU17' (U.S. Plant Pat. No. 16,978) in Marslev, Denmark. The female parent, 'Akzawhir' has a white flower color with purple at the petal base and a compact and mounding plant habit. The male parent, 'Kakegawa AU17' has a white flower color, violet disc florets and a very compact plant habit.

In May 2006 the two *Osteospermum* parental lines 'Akzawhir' and 'Kakegawa AU17' were crossed and seeds were obtained. The seeds were sown and plants were grown in pots for evaluation. In February 2007 a plant line was selected which had pure, clean, white ray florets and blue disc florets with medium sized flowers and a compact, mounding and well branching plant growth habit.

In February 2007, the line was vegetatively propagated by cuttings and re-evaluated in an open field and a greenhouse. The selected line was given the breeder code number '208009' and the stability of the distinct characteristics of this variety were confirmed.

In June 2007, plants of line '208009' were evaluated again in pots and in an open field. The variety was found to reproduce true to type in successive generations of asexual propagation via vegetative cuttings and given the name 'SAKOST8330'.

SUMMARY

The following are the most outstanding and distinguishing characteristics of this new variety when grown under normal horticultural practices in Salinas, Calif.

1. White ray florets and blue disc florets;
2. Medium sized flowers; and
3. A compact, mounding and well branching plant growth habit.

DESCRIPTION OF THE PHOTOGRAPHS

This new *Osteospermum* plant is illustrated by the accompanying photographs which show the plant's overall plant habit including form, foliage, and flowers. The photographs are of a twelve months old plant from transplant grown in 8-inch pots from rooted cuttings in Salinas, Calif. under greenhouse conditions in the fall of 2012. The colors shown are as true as can be reasonably obtained by conventional photographic procedures.

DESCRIPTION OF THE NEW VARIETY

Figure 1:
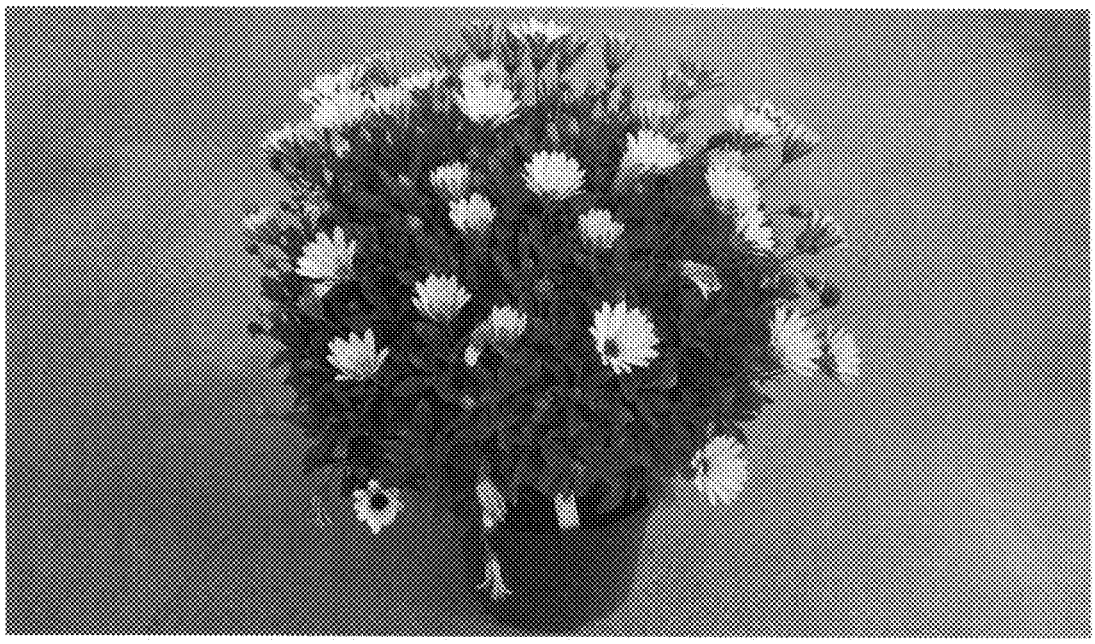
FIG. 1 shows the overall plant habit of the plant grown in a pot.
Figure 2:
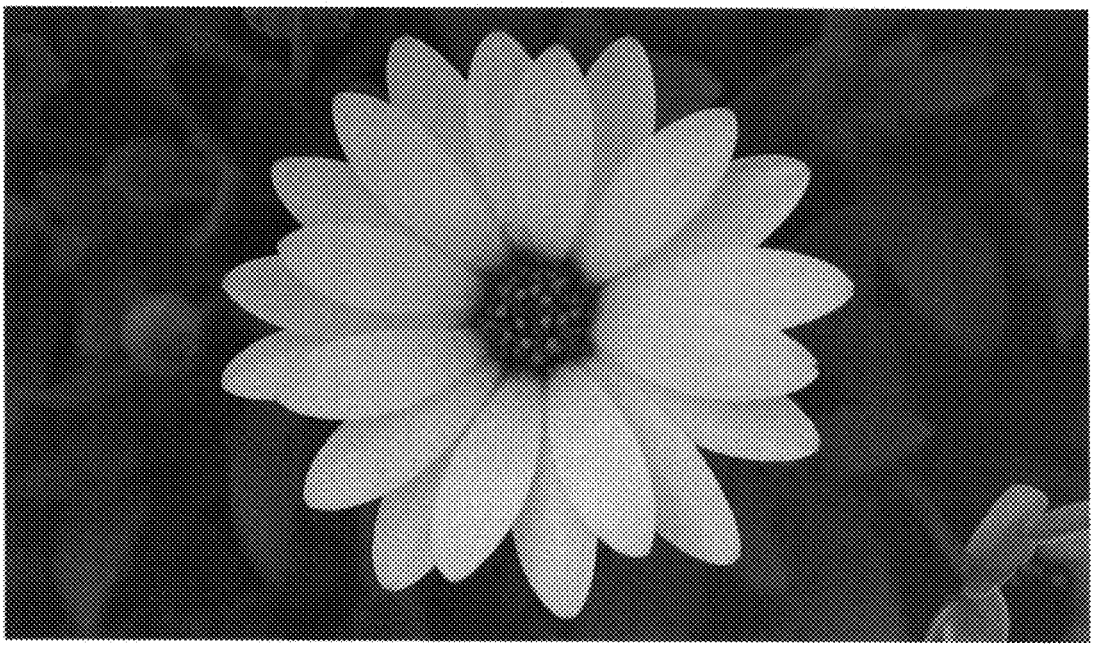
FIG. 2 shows the mature inflorescence of the plant.

The following detailed descriptions set forth the distinctive characteristics of 'SAKOST8330'. The data which define these characteristics were collected from asexual reproductions carried out in Salinas, Calif. Data was collected on twelve-month-old plants from transplant grown in 8-inch pots from rooted cuttings in Salinas, Calif. under greenhouse conditions in the fall of 2012. Color references are to The R.H.S. Colour Chart of The Royal Horticultural Society of London (R.H.S.), $4^{th}$ edition. Anatomic labels are from The Cambridge Illustrated Glossary of Botanical Terms, by M. Hickey and C. King, Cambridge University Press.

Classification:

*Family*.—Compositae.

*Botanical*.—*Osteospermum hybrida*.

*Common*.—*Osteospermum*, Cape Daisy, South African Daisy.

*Designation*.—'SAKOST8330'.

Parentage:

*Female parent*.—The proprietary *Osteospermum* line 'Akzawhir' (unpatented).

*Male parent*.—The *Osteospermum* line 'Kakegawa AU17' (U.S. Plant Pat. No. 16,978).

Growth:

*Time to produce a rooted cutting*.—Cuttings will colonize a 2.5 cm diameter by 2.5 cm tall greenhouse tray cell with peat-based plant media in approximately four weeks. Cuttings are dipped in a normal dilution (1:9) of Dip 'N Grow root inducing solution in water. The trays are misted hourly during rooting.

*Environmental conditions for plant growth*.—Rooted cuttings are transplanted to pots with a 16 cm diameter, one plant per pot. Peat-based growing media is used. The pots are watered using a 150 ppm to 200 ppm fertilizer solution using 18-8-18 fertilizer. The soil is allowed to dry between watering. During the first few weeks after transplanting, the plants should have evening temperatures around 15° C. to 18° C. for good root growth. When plants reach 7.5 cm to 10 cm in height they are pinched back to 5 to 6 leaves to promote branching. Spring and summer daytime high temperatures in Salinas, Calif. where the data was collected, range from 16° C. to 25° C.

*Time to bloom from propagation*.—Approximately four weeks when rooted vegetative cuttings are transferred to a 5-inch diameter pot. Flowering season is in the spring, summer and fall in the United States. Vernalization is not required to induce flowering.

Plant description:

*Habit*.—Compact, mounding and well-branching.

*Life cycle*.—Perennial.

*Form*.—Semi-erect.

*Height* (*from soil line to first node*).—2.0 cm.

*Height* (*from soil line to top of foliage*).—30.0 cm.

*Width*.—60.0 cm.

Stems:

*General*.—Multiple; circular in cross-section.

*Stem length* (*total*).—17.0 cm.

*Diameter*.—0.4 cm.

*Internode length*.—2.0 cm.

*Color*.—RHS 144B (Yellow-Green).

*Pubescence*.—Light. Color: RHS N155A (White). Shape: Short, hair-like fibers.

*Anthocyanin color*.—Absent.

Branches:

*General*.—Circular in cross-section.

*Number of main branches*.—One.

*Total number of branches*.—Four.

*Length*.—24.0 cm, approximately 2.0 cm from soil line to first node, 3.0 cm between first and second nodes.

*Diameter*.—1.0 cm.

*Internode length*.—3.0 cm.

*Color*.—RHS 144B (Yellow-Green).

*Pubescence*.—Absent.

*Anthocyanin color*.—Absent.

Leaves:

*Arrangement*.—Alternate.

*Shape*.—Oblanceolate.

*Apex*.—Acute.

*Base*.—Attenuate.

*Margin*.—Serrate.

*Venation*.—Pinnate.

*Surface* (*both surfaces*).—Dull.

*Surface pubescence* (*both surfaces*).—Slight.

*Surface pubescence color*.—RHS N155A (White).

*Attachment*.—Decurrant.

*Length*.—5.0 cm.

*Width*.—2.0 cm.

*Thickness*.—Less than 0.1 cm.

*Color*.—Upper surface: RHS 137A (Green). Lower surface: RHS 137B (Green).

*Venation color*.—Upper surface: RHS 144A (Yellow-green). Lower surface: RHS 144A (Yellow-green).

Inflorescence:

*Number per plant*.—40 to 50 in bloom.

*Type*.—Capitulum (head); disc florets are perfect and ray florets are carpellate.

*Flowering habit*.—Determinate.

*Lastingness of inflorescence on plant*.—3 to 4 days.

*Fragrance*.—Absent.

*Seed production*.—None observed.

*Diameter*.—5.0 cm.

*Depth*.—2.5 cm.

*Petal* (*ray floret*) *number*.—17 per inflorescence.

*Disc diameter*.—1.2 cm.

*Disc floret number*.—40 to 60 per inflorescence.

*Peduncle length*.—5.0 cm from inflorescence to first node.

*Peduncle diameter*.—0.15 cm.

*Peduncle color*.—RHS 144A (Green).

*Peduncle texture*.—Dull; slight pubescence.

*Phyllaries*.—Arrangement: 17 per inflorescence; free; arranged symmetrically. Length: 1.0 cm. Width: 0.2 cm. Apex: Acute. Margin: Entire. Shape: Linear; acute. Color: Upper surface: RHS 143A (Green). Lower surface: RHS 143B (Green).

Ray florets (ligules):

*Corolla*.—One petal per ray floret; only the outer row of florets are the ray florets.

*Number of ray florets*.—21 per inflorescence.

*Length*.—3.2 cm.

*Width*.—0.8 cm.

*Shape*.—Lanceolate.

*Apex*.—Acute.

*Margin*.—Entire.

*Color*.—Upper surface: RHS N155A (White). Lower surface: RHS 97B (Violet-Blue).

*Pubescence*.—Glabrous.

Disc florets:

*Color*.—RHS 94A (Violet-Blue).

*Shape*.—Tubular.

*Apex*.—Pointed.

*Texture*.—Dull, pubescent.

*Size*.—Length: 0.8 cm. Width: 0.1 cm.

Reproductive organs:

*Ovary*.—Superior.

*Pistil form*.—One style with two stigma branches.

*Pistil length*.—0.5 cm.

*Stigma color*.—RHS N92A (Violet-Blue).

*Style color*.—RHS 94C (Violet-Blue).

*Stamens*.—5; fused into a single tube.
*Anther color*.—RHS 187A (Greyed-Purple).
*Pollen color*.—RHS 17A (Yellow-Orange).
*Filament color*.—RHS 155A (White).

Disease and insect resistance: No known resistance or susceptibility.

COMPARISON WITH PARENTAL LINES AND KNOWN VARIETY

'SAKOST8330' is a distinct variety of *Osteospermum* is a distinct variety of *Osteospermum* owing to its pure clean white ray florets and blue disc florets with medium sized flower and a compact, mounding and well branching plant growth habit 'SAKOST8330' is distinguished from its parent as described in Table 1 (color references are to The Royal Horticultural Society Colour Chart, 4$^{th}$ edition):

TABLE 1

Comparison with Parental Lines

| Characteristic | 'SAKOST8330' | Female Parent 'Akzawhir' | Male Parent 'Kakegawa AU17' |
|---|---|---|---|
| Ray floret (ligule) color, upper surface: | RHS N155A (White) | White with purple at petal base | RHS 155A (White) with RHS 77B (Purple) at base |
| Plant growth habit: | Compact, mounding and well-branching | Compact and mounding | More compact and well-branching |

'SAKOST8330' is a distinct variety of *Osteospermum* owing to pure clean white ray florets and blue disc florets with medium sized flower and a compact, mounding and well branching plant growth habit. 'SAKOST8330' is most similar to the *Osteospermum* plant named 'Kakegawa AU17' (U.S. Plant Pat. No. 16,978). Differences between the two varieties are described in Table 2 (color references are to The Royal Horticultural Society Colour Chart, 4$^{th}$ edition):

TABLE 2

Comparison with Similar Variety

| Characteristic | 'SAKOST8330' | 'Kakegawa AU17' |
|---|---|---|
| Ray floret (ligule) color, upper surface: | RHS N155A (White) | RHS 155A (White) with RHS 77B (Purple) at base |
| Ray floret (ligule) color, lower surface: | RHS 97B (Violet-Blue) | RHS 82B (Purple-Violet) with RHS 155A (White) at edge RHS 77C (Purple) outer stripes and RHS 77A (Purple) inner stripes |
| Plant growth habit: | Compact, mounding and well-branching | More compact and well-branching |

I claim:

1. A new and distinct variety of *Osteospermum* plant as shown and described herein.

* * * * *